(12) United States Patent
Kassiou et al.

(10) Patent No.: US 11,472,774 B2
(45) Date of Patent: Oct. 18, 2022

(54) ANTI-CANCER COMPOUNDS

(71) Applicant: The University of Sydney, New South Wales (AU)

(72) Inventors: Michael Kassiou, New South Wales (AU); William Jorgensen, New South Wales (AU); Lenka Munoz, New South Wales (AU)

(73) Assignee: THE UNIVERSITY OF SYDNEY, New South Wales (AU)

(*) Notice: Subject to any disclaimer, the term of this patent is extended or adjusted under 35 U.S.C. 154(b) by 9 days.

(21) Appl. No.: 16/965,398

(22) PCT Filed: Feb. 1, 2019

(86) PCT No.: PCT/AU2019/050073
§ 371 (c)(1),
(2) Date: Jul. 28, 2020

(87) PCT Pub. No.: WO2019/148244
PCT Pub. Date: Aug. 8, 2019

(65) Prior Publication Data
US 2021/0094915 A1    Apr. 1, 2021

(30) Foreign Application Priority Data
Feb. 1, 2018  (AU) ................. 2018900315

(51) Int. Cl.
*C07D 213/75*    (2006.01)
*C07D 213/82*    (2006.01)
(Continued)

(52) U.S. Cl.
CPC ........ *C07D 213/75* (2013.01); *C07D 213/82* (2013.01); *C07D 241/24* (2013.01); *C07D 307/66* (2013.01); *C07D 317/66* (2013.01)

(58) Field of Classification Search
CPC .. C07D 213/75; C07D 213/82; C07D 241/24; C07D 307/66; C07D 317/66
See application file for complete search history.

(56) References Cited

U.S. PATENT DOCUMENTS

2006/0035938 A1* 2/2006 Bladh ................. A61P 11/06
                                            514/346
2019/0169127 A1* 6/2019 Lin .................... C07D 413/12

FOREIGN PATENT DOCUMENTS

DE    1238920 B     4/1967
WO    2001012189 A1  2/2001
(Continued)

OTHER PUBLICATIONS

Priority document for US2019/0169127 with EF date of Dec. 6, 2017.*

(Continued)

*Primary Examiner* — Valerie Rodriguez-Garcia
(74) *Attorney, Agent, or Firm* — Troutman Pepper Hamilton Sanders LLP

(57) ABSTRACT

The present invention relates to new pharmaceutical agents, and to their use in the treatment of proliferative diseases, such as cancer (in particular, brain cancer). In some embodiments, the present invention relates to compounds of formula (I):

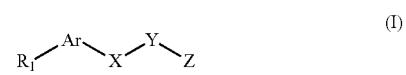

or pharmaceutically acceptable salts or prodrugs thereof.

11 Claims, 5 Drawing Sheets

(51) Int. Cl.
*C07D 241/24* (2006.01)
*C07D 307/66* (2006.01)
*C07D 317/66* (2006.01)

(56) References Cited

FOREIGN PATENT DOCUMENTS

| WO | 2001014353 | A1 | 3/2001 |
|---|---|---|---|
| WO | 2001068652 | A1 | 9/2001 |
| WO | 2004060281 | A2 | 7/2004 |
| WO | 2005054199 | A1 | 6/2005 |
| WO | 2005116009 | A1 | 12/2005 |
| WO | 2006108640 | A1 | 10/2006 |
| WO | 2008005457 | A2 | 1/2008 |
| WO | 2009006404 | A2 | 1/2009 |
| WO | 2011022473 | A1 | 2/2011 |
| WO | 2011113606 | A1 | 9/2011 |
| WO | 2013014587 | A2 | 1/2013 |
| WO | 2013032907 | A1 | 3/2013 |
| WO | 2013076230 | A1 | 5/2013 |
| WO | 2013143597 | A2 | 10/2013 |
| WO | 2016055786 | A1 | 4/2016 |
| WO | 2016067009 | A1 | 5/2016 |
| WO | WO 2016-066574 | * | 5/2016 |
| WO | 2016119017 | A1 | 8/2016 |
| WO | 2016193939 | A1 | 12/2016 |
| WO | 2019/113242 | A1 | 6/2019 |

OTHER PUBLICATIONS

Communication (International Search Report) received in International Application No. PCT/AU2019/050073 dated Apr. 1, 2019, 11 pages total.
Communication (Written Opinion) received in International Application No. PCT/AU2019/050073 dated Apr. 1, 2019, 6 pages total.
Brocklehurst, K.J. et al., "Discovery, Optimisation and in vivo Evaluation of Novel GPR119 Agonists," Bioorganic & Medicinal Chemistry Letters (2011) vol. 21, No. 24, pp. 7310-7316.
CAS Registry No. 1607369-88-9; Entered STN May 21, 2014; 3-Pyrrolidinecarboxamide, N-ethyl-3-fluoro-N-[[4-(4-methoxy-1-piperidinyl)phenyl]methyl]-, hydrochloride (1:2).
CAS Registry No. 2040740-98-3; Entered STN: Nov. 30, 2016; 2H-Pyran-4-carboxamide, 4-(aminomethyl)tetrahydro-N-methyl-N-[[2-( 1-pyrrolidinyl)phenyl ]methyl]-.
CAS Registry No. 1841021-36-0; Entered STN Jan. 7, 2016; 2-Propenamide, N-(6-amino-1,3-benzodioxol-5-yl)-3-[4-(1H-imidazol-1-yl)phenyl]-, hydrochloride (1:2).

English translation of JP Communication for Japanese Application No. 2020-541480, dated Aug. 31, 2021, 10 pages total.
Nozaki, Masakatsu et al., Medicinal Chemistry, Kagaku-Dojin Publishing Co., Inc. (1995) pp. 98-99, 12 pages total.
RN 1587725-56-1 Registry, Database Registry (online) Retrieved from STN, Apr. 21, 2014, Supplier: FCH Group, Search Date: Aug. 4, 2021, N-(6-amino-3-pyridinyl)-3-(4-fluorophenyl)-1,2,4-oxadiazole-5-butanamide monohydrochloride, 1 page total.
Wermuth, C.G., "The Practice of Medicinal Chemistry: Chapter 13, Toka chikan ni motozuku bunshi no henkan [Conversion of molecules based on equivalent substitutions]," Technomics, Inc. (1998) pp. 235-271, 48 pages total.
Parella, R. & Babu, S. A., "Pd(II)-Catalyzed, Picolinamide-Assisted, Z Selective γ Arylation of Allylamines to Construct Z Cinnamylamines", Journal of Organic Chemistry, 2017, vol. 82, pp. 6550-6567.
CAS Registry No. 1626892-47-4; STN Entry date Sep. 26, 2014; 1,2,4-Oxadiazole-5-butanamide, 3-(4-chlorophenyl)-N-(4,5,6,7-tetrahydro-4-benzofuranyl)-.
CAS Registry No. 1298216-52-0; STN Entry date May 22, 2011; 1,2,4-Oxadiazole-5-butanamide, N-(3-iodo-2-pyridinyl)-3-(4-methoxyphenyl)-.
CAS Registry No. 1214551-73-1; STN Entry date Mar. 25, 2010; 4-Pyridinecarboxamide, N-[3-[2-(4-fluorophenyl)-1H-pyrrolo[2,3-b]pyridin-1-yl]propyl]-.
CAS Registry No. 1797902-29-4; STN Entry Date Jul. 9, 2015; 1H-Pyrazole-3-carboxamide, N-[3-[3-(4-fluorophenyl)-1,2,4-oxadiazol-5-yl]propyl]-.
CAS Registry No. 1348166-75-5; STN Entry date Dec. 4, 2011; 2-Benzofurancarboxamide, 5-[(4-[1,1'-biphenyl]-4-yl-1-oxobutyl)amino]-N-hydroxy-.
CAS Registry No. 1102234-44-5; STN Entry date Feb. 8, 2009; 4-Pyridinecarbothioamide, N-(3-[1,1'-biphenyl]-4-ylpropyl)-2,6-dichloro-.
CAS Registry No. 1102230-83-0; STN Entry date Feb. 8, 2009; Methanethione, [(3-[1,1'-biphenyl]-4-ylpropyl)amino](3,4-dichloro-5-isothiazolyl)-.
CAS Registry No. 1909524-80-6; STN Entry Date May 13, 2016; Benzenebutanamide, 4-chloro-N-(2-chloro-3-pyridinyl)-.
CAS Registry No. 1907267-48-4; STN Entry date May 10, 2016; Benzenebutanamide, 4-chloro-N-6-[(1-methylethyl)amino]-3-pyridinyl]-.
CAS Registry No. 1216855-58-1; STN Entry Date Apr. 5, 2010; Benzenebutanamide, 4-fluoro-N-(6-methoxy-3-pyridinyl)-.
CAS Registry No. 1901779-58-5; STN Entry date May 2, 2016; Benzenebutanamide, 4-chloro-N-3-pyridinyl-.
Australian Examination Report No. 2 for AU Application No. 20192155799 dated Mar. 28, 2022 // Applicant Name: The University of Sydney // 19 pages.

* cited by examiner

ANTI-CANCER COMPOUNDS

CROSS-REFERENCE TO RELATED APPLICATIONS

This application is a National Stage application of International Application No. PCT/AU2019/050073, filed Feb. 1, 2019, which claims priority to Australian Patent Application No. 2018900315, filed Feb. 1, 2018, all of which are hereby incorporated by reference in their entireties.

FIELD OF THE INVENTION

The present invention relates to pharmaceutical agents, and to their use in the treatment of proliferative diseases, such as cancer (in particular, brain cancer).

BACKGROUND OF THE INVENTION

Current methods of treating solid cancers of the brain (i.e. brain tumours) involve one or more of surgery, radiation therapy and chemotherapy. For example, glioblastoma (which is the most common brain cancer in humans) is treated using the Stupp protocol. This involves concomitant radiation/temozolomide-based chemotherapy, followed by adjuvant chemotherapy with temozolomide alone, and is carried out after maximal surgical resection of the tumour. Temozolomide prolongs survival by approximately three months (compared to radiation alone) and the median survival of glioblastoma patients is 15 months. Avastin has been approved for recurrent glioblastomas, but has resulted in little improvement in survival.

Further, even though 50% of glioblastomas are dependent on epidermal growth factor receptor (EGFR) signalling, the clinically available EGFR inhibitors have failed in glioblastoma clinical trials. Some inhibitors did not have sufficient Blood-Brain Barrier (BBB) permeability. Recent studies have also revealed that glioblastomas respond only to type II EGFR inhibitors, whereas type I inhibitors were trialled. Extreme heterogeneity and invasiveness of glioblastomas has also contributed to the failure of molecularly-targeted therapies as effective treatments for brain cancers.

Another class of compounds that has been shown to be effective in a number of non-brain cancers are the tubulin-targeting chemotherapeutics. However, the tubulin inhibitors that are clinically used (e.g. Taxol) are very large molecules that are not able to penetrate the BBB. In addition, Taxol and other tubulin-targeting chemotherapeutics (such as vinblastine and vincristine) have serious side effects (e.g. chemotherapy-induced peripheral neuropathy).

Therefore, there is a need to find new treatments for proliferative diseases, such as cancer, and in particular to find effective treatments for brain cancers.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention seeks to address one or more of the above mentioned problems, and/or to provide improvements in cancer therapy and, in a first aspect, provides a compound of formula (I):

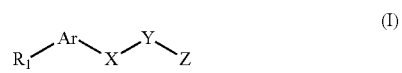

or a pharmaceutically acceptable salt or prodrug thereof, wherein:

X is $C_1$-$C_6$ alkyl or $C_2$-$C_6$ alkenyl;

Y is

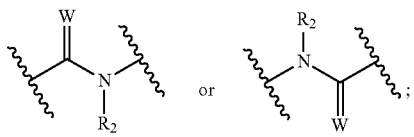

W is O or S;

$R_2$ is H, alkyl or alkenyl;

Z is an aryl, heterocycloalkyl or heteroaryl group, which aryl, heterocycloalkyl or heteroaryl group is optionally substituted;

$R_1$ is a halo, cycloalkyl, heterocycloalkyl, aryl or heteroaryl group, which cycloalkyl, heterocycloalkyl, aryl or heteroaryl group is optionally substituted;

Ar is an aryl or heteroaryl group.

X may be $C_3$ alkyl or $C_3$ alkenyl.

W may be O.

$R_1$ may be an aryl group. The aryl group may be monocyclic or bicyclic. The aryl group may be phenyl or naphthyl. The aryl group may be substituted. The substituent may be selected from a halo group and a heteroalkyl group. The halo group may be F, the heteroalkyl group may be O-alkyl (e.g. —$OCH_3$) or aminoalkyl (e.g. —$CH_2NH_2$).

$R_1$ may be a heteroaryl group. The heteroaryl group may be monocyclic or bicyclic. The heteroaryl group may include one or more nitrogen atoms. For example, the heteroaryl group may be pyrazole, isoxazole, triazole, pyridine, pyrimidine, quinoline, benzimidazole or indole. The heteroaryl group may be substituted. For example, the substituent may be a halo group (e.g. F) or a heteroalkyl group (e.g. O-alkyl, such as —$OCH_3$, or aminoalkyl, such as —$CH_2NH_2$).

$R_1$ may be a heterocycloalkyl group. The heterocycloalkyl group may include one or more nitrogen atoms. The heterocycloalkyl group may be piperazine. The heterocycloalkyl group may include one or more oxygen atoms (in addition to, or as an alternative to, one or more nitrogen atoms). The heterocycloalkyl group may be morpholine. The heterocycloalkyl group may be substituted by, for example, a halo group (e.g. F) or a heteroalkyl group (e.g. O-alkyl, such as —$OCH_3$, or aminoalkyl, such as —$CH_2NH_2$).

Ar may be an aryl group. The aryl group may be phenyl. Ar may be a heteroaryl group. The heteroaryl group may include one or more nitrogen atoms and/or NH groups. The heteroaryl group may have 4 or 5 ring carbon atoms. The heteroaryl group could be pyridine or pyrimidine.

Z may be an aryl group. The aryl group may be monocyclic or bicyclic. For example, the aryl group may be phenyl. The aryl group may be substituted. The substituent may be a heteroalkyl group. The heteroalkyl group may include one or more oxygen atoms. The heteroalkyl group may form a ring with the aryl group.

Z may be a heteroaryl group. The heteroaryl group may be monocyclic or bicyclic. The heteroaryl group may include one or more nitrogen atoms. For example, the heteroaryl group may be pyrazole, isoxazole, triazole, pyridine, pyrimidine, pyrazine, quinoline, benzimidazole or indole. The heteroaryl group may include one or more oxygen atoms (in addition to, or as an alternative to, one or more nitrogen atoms). For example, the heteroaryl group may be furan. The heteroatom may be at one or more positions on the ring or rings. For example, when Z is a pyridine group, the nitrogen may be at one or more positions on the ring. For example, the nitrogen may be at the meta position. The nitrogen may be at the ortho position and/or at one or more of the meta and/or para positions. The heteroaryl group may be substituted. For example, the substituent may be a hydroxyl, a halo group (e.g. F) or a heteroalkyl group (e.g. O-alkyl, such as —OCH$_3$, or aminoalkyl, such as —CH$_2$NH$_2$).

Z may be a heterocycloalkyl group. The heterocycloalkyl group may include one or more nitrogen atoms. The heterocycloalkyl group may be piperazine. The heterocycloalkyl group may include one or more oxygen atoms (in addition to, or as an alternative to, one or more nitrogen atoms). The heterocycloalkyl group may be morpholine. The heterocycloalkyl group may be partially unsaturated. The heterocycloalkyl group may be substituted by, for example, a hydroxyl, a halo group (e.g. F) or a heteroalkyl group (e.g. O-alkyl, such as —OCH$_3$, or aminoalkyl, such as —CH$_2$NH$_2$).

R$_2$ may be H, alkyl or alkenyl. R$_2$ may be H.

The compound of formula (I) may be selected from:

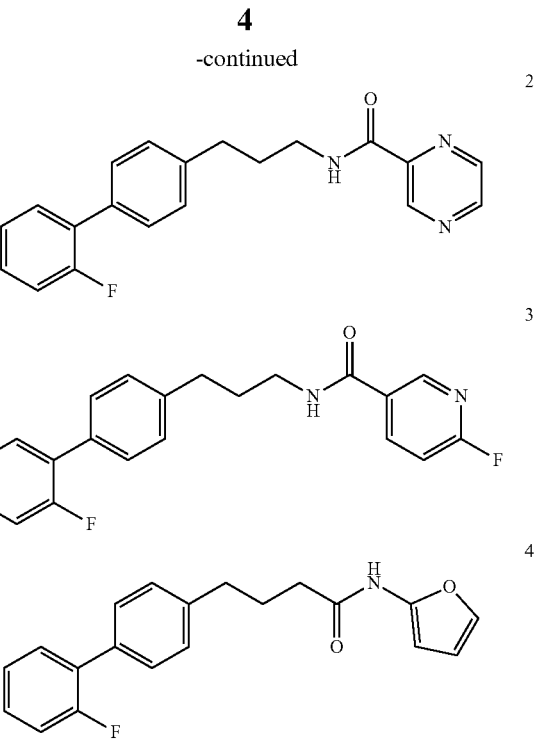

In a second aspect, the present invention relates to a pharmaceutical composition including a compound of formula (I) (according to the first aspect of the invention) together with a pharmaceutically acceptable excipient.

Compounds and pharmaceutical compositions according to the present invention may be suitable for the treatment or prevention of a proliferative disease. Accordingly, in another aspect, the present invention relates to a method of treating or preventing a proliferative disease in a subject, the method including administering to the subject an effective amount of a compound of formula (I) according to the first aspect of the invention or a pharmaceutical composition according to the second aspect of the invention.

In a further aspect the present invention relates to the use of a compound of formula (I) according to the first aspect of the invention or a pharmaceutical composition according to the second aspect of the invention in the manufacture of a medicament for treating or preventing a proliferative disease.

In a further aspect the present invention relates to the use of a compound of formula (I) according to the first aspect of the invention or a pharmaceutical composition according to the second aspect of the invention for the treatment or prevention of a proliferative disease in a subject.

In a further aspect the present invention relates to a compound of formula (I) according to the first aspect of the invention or a pharmaceutical composition according to the second aspect of the invention for use in the treatment or prevention of a proliferative disease in a subject.

In one embodiment, the proliferative disease is cancer. The cancer may be selected from the group consisting of brain cancer, breast cancer, lung cancer, prostate cancer, ovarian cancer, uterine cancer, skin cancer, colon cancer and bladder cancer.

The cancer may be primary. The cancer may be metastatic. The cancer may be benign. The cancer may be malignant.

The cancer may be brain cancer (e.g. anaplastic astrocytoma, astrocytoma, central neurocytoma, choroid plexus carcinoma, choroid plexus papilloma, choroid plexus tumour, diffuse intrinsic pontine glioma, dysembryoplastic neuroepithelial tumour, ependymal tumour, fibrillary astrocytoma, giant-cell glioblastoma, glioblastoma multiforme, gliomatosis cerebri, gliosarcoma, hemangiopericytoma, medulloblastoma, medulloepithelioma, meningeal carcinomatosis, neuroblastoma, neurocytoma, oligoastrocytoma, oligodendroglioma, optic nerve sheath meningioma, pediatric ependymoma, pilocytic astrocytoma, pinealoblastoma, pineocytoma, pleomorphic anaplastic neuroblastoma, pleomorphic xanthoastrocytoma, primary central nervous system lymphoma, sphenoid wing meningioma, subependymal giant cell astrocytoma, subependymoma, trilateral retinoblastoma). The brain cancer may be a primary cancer (e.g. a glioma, a meningioma, a pituitary adenoma or a nerve sheath tumour). The brain cancer may be a metastatic cancer (e.g. a result of melanoma or lung cancer).

In a further aspect, the present invention relates to a method of completely or partially preventing the recurrence of a solid tumour in a subject, the method including administering to the subject an effective amount of a compound of formula (I) according to the first aspect of the invention or a pharmaceutical composition according to the second aspect of the invention.

In another aspect the invention relates to the use of a compound according to the first aspect of the invention or the pharmaceutical composition according to the second aspect of the invention in the manufacture of a medicament for completely or partially preventing the recurrence of a solid tumour.

In a further aspect the present invention relates to the use of a compound of formula (I) according to the first aspect of the invention or a pharmaceutical composition according to the second aspect of the invention for completely or partially preventing the recurrence of a solid tumour in a subject.

In a further aspect the present invention relates to a compound of formula (I) according to the first aspect of the invention or a pharmaceutical composition according to the second aspect of the invention for use in completely or partially preventing the recurrence of a solid tumour in a subject.

The solid tumour may be a brain cancer (e.g. glioblastoma, astrocytoma, or glioma). The brain cancer may be a primary cancer. The brain cancer may be a metastatic cancer.

The compounds of formula (I) may be used in therapy alone or in combination with one or more other therapeutic agents, for example, as part of a combination therapy.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
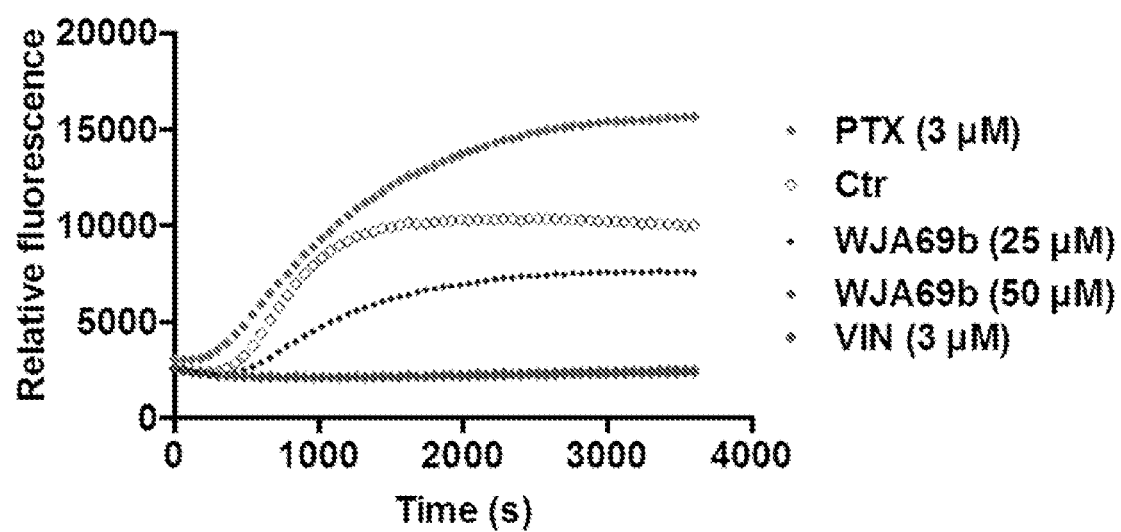
FIG. 1. Results of an in vitro tubulin polymerization assay using WJA69b.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Therefore, as used herein, the singular forms "a", "an" and "the" include plural aspects, and vice versa, unless the context clearly dictates otherwise. For example, reference to "a" includes a single as well as two or more; reference to "an" includes a single as well as two or more; reference to "the" includes a single as well as two or more and so forth.

The invention is based on the surprising finding that compounds of formula (I) provide unexpected improvement in the treatment of proliferative diseases, such as cancer, and especially brain cancers.

Compounds are generally described herein using standard nomenclature. For compounds having asymmetric centres, it will be understood that, unless otherwise specified, all of the optical isomers and mixtures thereof are encompassed. Compounds with two or more asymmetric elements can also be present as mixtures of diastereomers. In addition, compounds with carbon-carbon double bonds may occur in Z and E forms, with all isomeric forms of the compounds being included in the present invention unless otherwise specified. Where a compound exists in various tautomeric forms, a recited compound is not limited to any one specific tautomer, but rather is intended to encompass all tautomeric forms. Recited compounds are further intended to encompass compounds in which one or more atoms are replaced with an isotope, i.e., an atom having the same atomic number but a different mass number. By way of general example, and without limitation, isotopes of hydrogen include tritium and deuterium and isotopes of carbon include $^{11}C$, $^{13}C$, and $^{14}C$.

Compounds according to the formula provided herein, which have one or more stereogenic centres, have an enantiomeric excess of at least 50%. For example, such compounds may have an enantiomeric excess of at least 60%, 70%, 80%, 85%, 90%, 95%, or 98%. Some embodiments of the compounds have an enantiomeric excess of at least 99%. It will be apparent that single enantiomers (optically active forms) can be obtained by asymmetric synthesis, synthesis from optically pure precursors, biosynthesis or by resolution of the racemates, for example, enzymatic resolution or resolution by conventional methods such as crystallization in the presence of a resolving agent, or chromatography, using, for example, a chiral HPLC column.

Certain compounds are described herein using a general formula that includes variables such as $R_1$, $R_2$, Ar, W, X, Y and Z. Unless otherwise specified, each variable within such a formula is defined independently of any other variable, and any variable that occurs more than one time in a formula is defined independently at each occurrence. Therefore, for example, if a group is shown to be substituted with 0, 1 or 2 R*, the group may be unsubstituted or substituted with up to two R* groups and R* at each occurrence is selected independently from the definition of R*. Also, combinations of substituents and/or variables are permissible only if such combinations result in stable compounds, i.e., compounds that can be isolated, characterized and tested for biological activity.

A "pharmaceutically acceptable salt" of a compound disclosed herein is an acid or base salt that is generally considered in the art to be suitable for use in contact with the tissues of human beings or animals without excessive toxicity or carcinogenicity, and preferably without irritation, allergic response, or other problem or complication. In particular, pharmaceutically acceptable salts in accordance with the present invention are those that do not adversely affect the ability of the compound to cross the BBB. Such salts include mineral and organic acid salts of basic residues such as amines, as well as alkali or organic salts of acidic residues such as carboxylic acids.

Suitable pharmaceutically acceptable salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzenesulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic (such as acetic, HOOC—$(CH_2)_n$—COON where n is any integer from 0 to 6, i.e. 0, 1, 2, 3, 4, 5 or 6), and the like. Similarly, pharmaceutically acceptable cations include, but are not limited to sodium, potassium, calcium, aluminum, lithium and ammonium. A person skilled in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent (such as ether, ethyl acetate, ethanol, isopropanol or acetonitrile), or in a mixture of the two.

It will be apparent that each compound of formula (I) may, but need not, be present as a hydrate, solvate or non-covalent complex. In addition, the various crystal forms and polymorphs are within the scope of the present invention, as are prodrugs of the compounds of formula (I) provided herein.

A "prodrug" is a compound that may not fully satisfy the structural requirements of the compounds provided herein, but is modified in vivo, following administration to a subject or patient, to produce a compound of formula (I) provided herein. For example, a prodrug may be an acylated derivative of a compound as provided herein. Prodrugs include compounds wherein hydroxy, carboxy, amine or sulfhydryl groups are bonded to any group that, when administered to a mammalian subject, cleaves to form a free hydroxy, carboxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

A "substituent" as used herein, refers to a molecular moiety that is covalently bonded to an atom within a molecule of interest. For example, a "ring substituent" may be a moiety such as a halogen, alkyl group, heteroalkyl group, haloalkyl group or other substituent described herein that is covalently bonded to an atom, preferably a carbon or nitrogen atom, that is a ring member. The term "substituted," as used herein, means that any one or more hydrogens on the designated atom is replaced with a selection from the indicated substituents, provided that the designated atom's normal valence is not exceeded, and that the substitution results in a stable compound, i.e., a compound that can be isolated, characterized and tested for biological activity. When a substituent is oxo, i.e., =O, then two hydrogens on the atom are replaced. An oxo group that is a substituent of an aromatic carbon atom results in a conversion of —CH— to —C(=O)— and a loss of aromaticity. For example a pyridyl group substituted by oxo is a pyridone. Examples of suitable substituents are alkyl (including haloalkyl e.g. $CF_3$), heteroalkyl (e.g. —$OCH_3$, —$CH_2NHCH_3$, —$CH_2NH_2$), halogen (for example, fluorine, chlorine, bromine or iodine atoms), OH, =O, SH, $SO_3H$, $NH_2$, =NH, $N_3$ and $NO_2$ groups.

The term "alkyl" refers to a saturated, straight-chain or branched hydrocarbon group. Specific examples of alkyl groups are methyl, ethyl, propyl, iso-propyl, n-butyl, iso-butyl, sec-butyl, tert-butyl, n-pentyl, iso-pentyl, n-hexyl and 2,2-dimethylbutyl.

The term "heteroalkyl" refers to an alkyl group as defined above that contains one or more heteroatoms selected from oxygen, nitrogen and sulphur (especially oxygen and nitrogen). Specific examples of heteroalkyl groups are O-alkyl groups, such as methoxy, trifluoromethoxy, ethoxy, n-propyloxy, iso-propyloxy, butoxy and tert-butyloxy, methoxymethyl, ethoxymethyl, —$CH_2CH_2OH$, —$CH_2OH$, methoxyethyl, 1-methoxyethyl, 1-ethoxyethyl, 2-methoxyethyl or 2-ethoxyethyl, aminoalkyl (such as —$CH_2NH_2$, —$CH_2CH_2NH_2$, etc) methylamino, ethylamino, propylamino, iso-propylamino, dimethylamino, diethylamino, iso-propylethylamino, methylamino methyl, ethylamino methyl, di-iso-propylamino ethyl, methylthio, ethylthio, iso-propylthio, enol ether, dimethylamino methyl, dimethylamino ethyl, acetyl, propionyl, butyryloxy, acetyloxy, methoxycarbonyl, ethoxycarbonyl, propionyloxy, acetylamino, propionylamino, carboxymethyl, carboxyethyl, carboxypropyl, N-ethyl-N-methylcarbamoyl and N-methylcarbamoyl. Further examples of heteroalkyl groups are nitrile, iso-nitrile, cyanate, thiocyanate, iso-cyanate, iso-thiocyanate and alkylnitrile groups.

The term "alkenyl" refers to an at least partially unsaturated, straight-chain or branched hydrocarbon group that contains at least two carbon atoms (i.e. $C_2$ alkenyl). Specific examples of alkenyl groups are ethenyl (vinyl), propenyl (allyl), iso-propenyl, butenyl, ethinyl, propinyl, butinyl, acetylenyl, propargyl, iso-prenyl and hex-2-enyl group. Preferably, alkenyl groups have one or two double bond(s).

The term "cycloalkyl" refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. Specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetraline, adamantane (i.e. tricycle [3.3.1.13,7]decane), cyclopentylcyclohexyl and cyclohex-2-enyl.

The term "heterocycloalkyl" refers to a cycloalkyl group as defined above in which one or more (preferably 1, 2 or 3) ring carbon atoms, each independently, have been replaced by an oxygen, nitrogen, silicon, selenium, phosphorus or sulfur atom (preferably by an oxygen, sulfur or nitrogen atom). This includes groups containing these atoms, such as NH. A heterocycloalkyl group has preferably 1 or 2 rings containing from 3 to 10 (especially 3, 4, 5, 6 or 7) ring atoms (preferably selected from C, O, N and S). Specific examples are piperidyl, prolinyl, imidazolidinyl, piperazinyl, morpholinyl, urotropinyl, pyrrolidinyl, tetrahydrothiophenyl, tetrahydropyranyl, tetrahydrofuryl and 2-pyrazolinyl group and also lactames, lactones, cyclic imides and cyclic anhydrides.

The term "aryl" refers to an aromatic group that contains one or more rings containing from 6 to 14 ring carbon atoms, preferably from 6 to 10 (especially 6) ring carbon atoms. Examples are phenyl, naphthyl and biphenyl groups.

The term "heteroaryl" refers to an aromatic group that contains one or more rings containing from 5 to 14 ring atoms, preferably from 5 to 10 (especially 5 or 6) ring atoms, and contains one or more (preferably 1, 2, 3 or 4) oxygen, nitrogen, phosphorus or sulfur ring atoms (preferably O, S or N). This includes O, S or N-containing groups, such as NH. Examples are pyridyl (for example, 4-pyridyl), imidazolyl (for example, 2-imidazolyl), phenylpyrrolyl (for example, 3-phenylpyrrolyl), thiazolyl, iso-thiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, iso-quinolinyl, pyrrolyl, purinyl, carbazolyl, acridinyl, pyrimidyl, 2,3'-bifuryl and pyrazolyl (for example, 3-pyrazolyl) groups.

The expression "halogen" or "halogen atom" as used herein means fluorine, chlorine, bromine, or iodine.

The term "optionally substituted" refers to a group in which one, two, three or more hydrogen atoms have been replaced independently of each other by halogen (for example, fluorine, chlorine, bromine or iodine atoms) and/or by, for example, OH, =O, SH, $SO_3H$, $NH_2$, N-alkyl, NH-alkyl, $N_3$ or $NO_2$ groups. This expression also refers to a group that is substituted by one, two, three or more alkyl, alkenyl or heteroalkyl (e.g. $-OCH_3$, $-OCH_2CH_3$, $-CH_2NHCH_3$ and $-CH_2NH_2$) groups. These groups may themselves be substituted. For example, an alkyl group substituent may be substituted by one or more halogen atoms (i.e. may be a haloalkyl group). The term "haloalkyl" refers to an alkyl group (as defined above) that is substituted by one or more halogen atoms (as also defined above). Specific examples of haloalkyl groups are trifluoromethyl, dichloroethyl, dichloromethyl and iodoethyl.

As used herein a wording defining the limits of a range of length such as, for example, "from 1 to 5" means any integer from 1 to 5, i.e. 1, 2, 3, 4 and 5. In other words, any range defined by two integers explicitly mentioned is meant to comprise and disclose any integer defining said limits and any integer comprised in said range.

Preferred compounds of formula (I) are those where X is $C_1$, $C_2$ or $C_3$ alkyl, or $C_2$ or $C_3$ alkenyl (e.g. $C_3$ alkyl or $C_3$ alkenyl).

$R_1$ may be an aryl group. The aryl group may be monocyclic or bicyclic. The aryl group may be phenyl or naphthyl. The aryl group may be substituted. The substituent may be selected from a halo group and a heteroalkyl group. The halo group may be F, and the heteroalkyl group may be O-alkyl (e.g. $OCH_3$ or $OCH_2CH_3$) or aminoalkyl (e.g. $-CH_2NH_2$ or $-CH_2CH_2NH_2$).

$R_1$ may be a heteroaryl group. The heteroaryl group may be monocyclic or bicyclic. The heteroaryl group may include one or more nitrogen atoms. For example, the heteroaryl group may be pyrazole, isoxazole, triazole, pyridine, pyrimidine, quinoline, benzimidazole or indole. The heteroaryl group may be substituted. For example, the substituent may be a halo group (e.g. F) or a heteroalkyl group (e.g. O-alkyl, such as $-OCH_3$ or $OCH_2CH_3$, or aminoalkyl, such as $-CH_2NH_2$ or $-CH_2CH_2NH_2$).

$R_1$ may be a heterocycloalkyl group. The heterocycloalkyl group may include one or more nitrogen atoms. The heterocycloalkyl group may be piperazine. The heterocycloalkyl group may include one or more oxygen atoms. The heterocycloalkyl group may be morpholine. The heterocycloalkyl group may be substituted by, for example, a halo group (e.g. F) or a heteroalkyl group (e.g. O-alkyl, such as $-OCH_3$ or $OCH_2CH_3$, or aminoalkyl, such as e.g. $-CH_2NH_2$ or $-CH_2CH_2NH_2$).

Ar may be an aryl group. The aryl group may be phenyl. Ar may be a heteroaryl group. The heteroaryl group may include one or more nitrogen atoms. The heteroaryl group may have 4 or 5 ring carbon atoms. The heteroaryl group may be pyridine or pyrimidine.

Z may be an aryl group. The aryl group may be monocyclic or bicyclic. For example, the aryl group may be phenyl. The aryl group may be substituted. The substituent may be an alkyl group, and alkene group or a heteroalkyl group. The heteroalkyl group may include one or more oxygen atoms, one or more amino groups, and/or one or more N-alkyl groups. The heteroalkyl group may form a ring with the aryl group.

Z may be a heteroaryl group. The heteroaryl group may be monocyclic or bicyclic. The heteroaryl group may include one or more nitrogen atoms. For example, the heteroaryl group may be pyrazole, isoxazole, triazole, pyridine, pyrimidine, pyrazine, quinoline, benzimidazole or indole. The heteroaryl group may include one or more oxygen atoms (in addition to, or as an alternative to, one or more nitrogen atoms). For example, the heteroaryl may be furan. The heteroatom may be at one or more positions on the ring or rings. For example, when Z is a pyridine group, the nitrogen may be at the meta position. The nitrogen may be at the ortho position and/or at one or more of the meta and/or para positions. The heteroaryl group may be substituted. For example, the substituent may be a hydroxyl, a halo group (e.g. F) or a heteroalkyl group (e.g. O-alkyl, such as $-OCH_3$, or aminoalkyl, such as $-CH_2NH_2$).

Z may be a heterocycloalkyl group. The heterocycloalkyl group may include one or more nitrogen atoms. The heterocycloalkyl group may be piperazine. The heterocycloalkyl group may include one or more oxygen atoms (in addition to, or as an alternative to, one or more nitrogen atoms). The heterocycloalkyl group may be morpholine. The heterocycloalkyl group may be partially unsaturated. The heterocycloalkyl group may be substituted by, for example, a hydroxyl, a halo group (e.g. F) or a heteroalkyl group (e.g. O-alkyl, such as —$OCH_3$, or aminoalkyl, such as —$CH_2NH_2$).

$R_2$ may be H, alkyl or alkenyl. $R_2$ may be H.

Specific examples of the compounds of the present invention are given in Table 1, below.

TABLE 1

Examples of compounds of the present invention

| Compound | Structure |
| --- | --- |
| WJA69b | 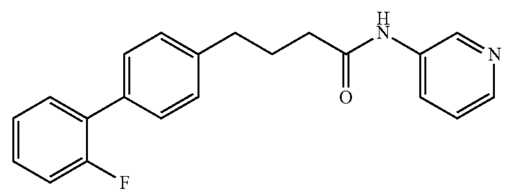 [SMILES: O=C(CCCc1ccc(-c2ccccc2F)cc1)Nc1cccnc1] |
| WJA88 | 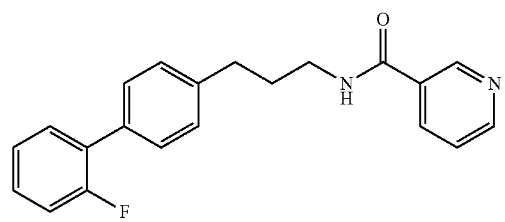 [SMILES: O=C(NCCCc1ccc(-c2ccccc2F)cc1)c1cccnc1] |
| WJA69c | 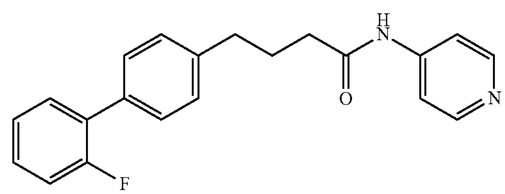 [SMILES: O=C(CCCc1ccc(-c2ccccc2F)cc1)Nc1ccncc1] |
| 1 | 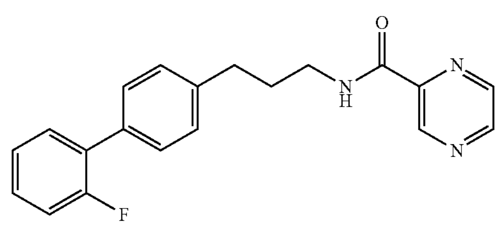 [SMILES: O=C(NCCCc1ccc(-c2ccccc2F)cc1)c1cnccn1] |
| 2 | 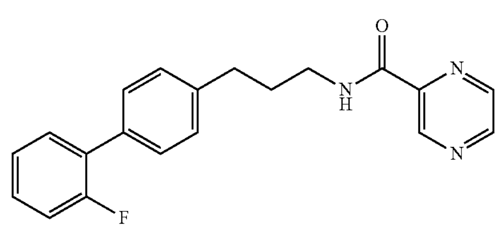 [SMILES: O=C(NCCCc1ccc(-c2ccccc2F)cc1)c1cnccn1] |
| 3 | 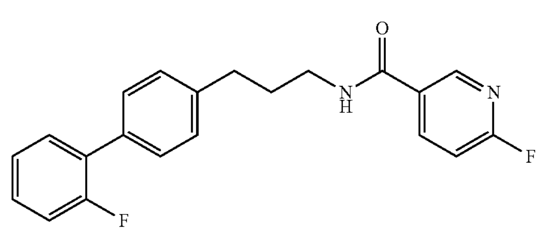 [SMILES: O=C(NCCCc1ccc(-c2ccccc2F)cc1)c1ccc(F)nc1] |

TABLE 1-continued

Examples of compounds of the present invention

| Compound | Structure |
|---|---|
| 4 | 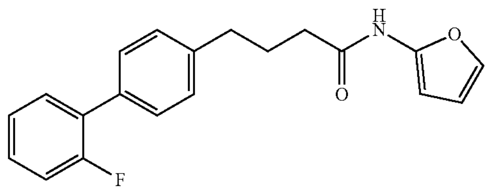 [SMILES: O=C(CCCc1ccc(-c2ccccc2F)cc1)Nc1ccco1] |
| 5 | 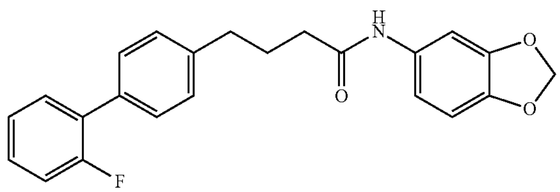 [SMILES: O=C(CCCc1ccc(-c2ccccc2F)cc1)Nc1ccc2c(c1)OCO2] |

In one embodiment, the compound of formula (I) is selected from the group consisting of compounds WJA69b, WJA88, WJA69c, 1, 2, 3, 4 and 5 from Table 1 above.

The compounds of the present invention can be synthesised by any suitable method known to a person skilled in the art. General syntheses are given below in Scheme 1.

The compounds of the present invention may exhibit high anti-proliferative activity and in particular, high efficacy against brain cancers. Specifically, in the examples herein, specific compounds are shown to induce apoptosis and are also able to cross the BBB.

Scheme 1. Examples of general syntheses of the compounds of the present invention

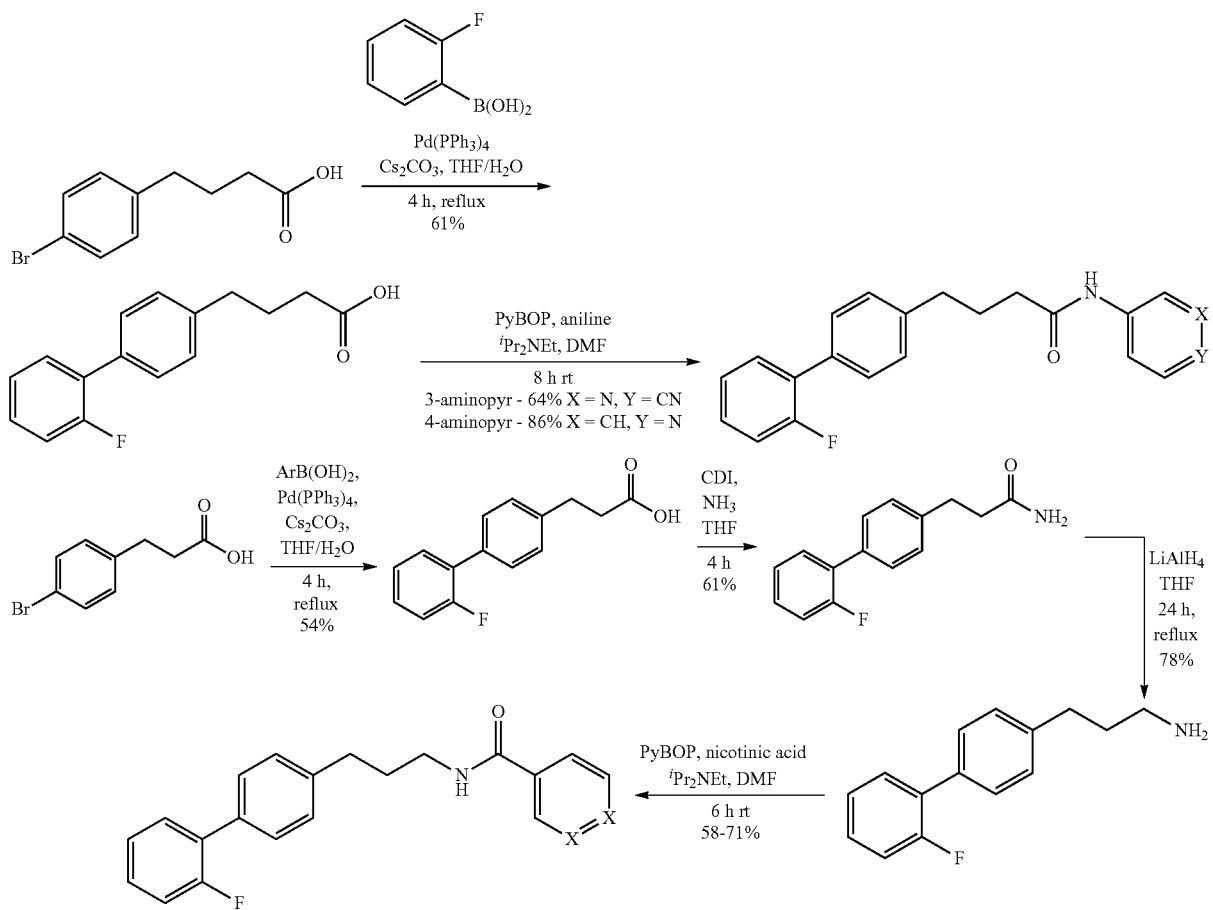

The therapeutic use of compounds of formula (I), their pharmaceutically acceptable salts, solvates, hydrates, prodrugs and also formulations and pharmaceutical compositions (including mixtures of the compounds of formula (I)) are within the scope of the present invention. Accordingly, the present invention also relates to pharmaceutical compositions including a therapeutically effective amount of a compound of formula (I), or its pharmaceutically acceptable salt, solvate, hydrate or prodrug, and one or more pharmaceutically acceptable excipients.

A "pharmaceutical carrier, diluent or excipient" includes, but is not limited to, any physiological buffered (i.e., about pH 7.0 to 7.4) medium including a suitable water soluble carrier, conventional solvents, dispersion media, fillers, solid carriers, coatings, antibacterial and antifungal agents, isotonic and absorption delaying agents. Suitable water soluble carriers include, but are not limited to saline, dextrose, corn oil, dimethylsulfoxide, and gelatin capsules. Other conventional additives include lactose, mannitol, corn starch, potato starch, binders such as crystalline cellulose, cellulose derivatives, acacia, gelatins, disintegrators such as sodium carboxymethyl-cellulose, and lubricants such as talc or magnesium stearate.

Pharmaceutical compositions may be formulated for any appropriate route of administration including, for example, topical (for example, transdermal or ocular), oral, buccal, nasal, vaginal, rectal or parenteral administration. The term "parenteral" as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. In certain embodiments, compositions in a form suitable for oral use or parenteral use are preferred. Suitable oral forms include, for example, tablets, troches, lozenges, aqueous or oily suspensions, dispersible powders or granules, emulsions, hard or soft capsules, or syrups or elixirs. For intravenous, intramuscular, subcutaneous, or intraperitoneal administration, one or more compounds may be combined with a sterile aqueous solution which is preferably isotonic with the blood of the recipient. Such formulations may be prepared by dissolving solid active ingredient in water containing physiologically compatible substances such as sodium chloride or glycine, and having a buffered pH compatible with physiological conditions to produce an aqueous solution, and rendering said solution sterile. The formulations may be present in unit or multi-dose containers such as sealed ampoules or vials. Examples of suitable components are described in Martindale—The Extra Pharmacopoeia (Pharmaceutical Press, London 1993) and Martin (ed.), Remington's Pharmaceutical Sciences.

For the treatment of proliferative disorders, the dose of the biologically-active compound according to the invention may vary within wide limits and may be adjusted to individual requirements. Active compounds according to the present invention are generally administered in a therapeutically effective amount. Preferred doses range from about 0.1 mg to about 140 mg per kilogram of body weight per day (e.g. about 0.5 mg to about 7 g per patient per day). The daily dose may be administered as a single dose or in a plurality of doses. The amount of active ingredient that may be combined with the carrier materials to produce a single dosage form will vary depending upon the host treated and the particular mode of administration. Dosage unit forms will generally contain between about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient), the severity of the particular disorder undergoing therapy, and the location of the unwanted proliferating cells. The dosage will generally be lower if the compounds are administered locally rather than systemically, and for prevention rather than for treatment. Such treatments may be administered as often as necessary and for the period of time judged necessary by the treating physician. A person skilled in the art will appreciate that the dosage regime or therapeutically effective amount of the compound of formula (I) to be administered may need to be optimized for each individual.

It will be appreciated that different dosages may be required for treating different disorders. An effective amount of an agent is that amount which causes a statistically significant decrease in neoplastic cell count, growth or size. Neoplastic disorders responsive to the agents of the present invention include, but are not limited to, brain cancer.

The terms "therapeutically effective amount" or "effective amount" refer to an amount of the compound of formula (I) that results in prevention, an improvement or remediation of the symptoms of a proliferative disorder. The dosage form and amount of the compounds or pharmaceutical compositions of the present invention can be readily established by reference to known treatment or prophylactic regimens.

Preferred compounds of the invention will have certain pharmacological properties. Such properties include, but are not limited to oral bioavailability and BBB permeability, such that the preferred oral dosage forms discussed above can provide therapeutically effective levels of the compound in vivo.

The compounds of the present invention are preferably administered to a patient (for example, a human) orally or parenterally, and are present within at least one body fluid or tissue of the patient. Accordingly, the present invention further provides methods for treating patients suffering from proliferative disorders (including cancer, such as brain cancer).

The terms "treating", "treatment" and "therapy" are used herein to refer to curative therapy. Therefore, in the context of the present disclosure, the term "treating" encompasses curing and ameliorating the severity of cancer or its associated symptoms.

"Preventing" or "prevention" means preventing the occurrence of the cancer or tempering the severity of the cancer if it develops subsequent to the administration of the compounds or pharmaceutical compositions of the present invention. This prevents the onset of clinically evident unwanted cell proliferation altogether or the onset of a preclinically evident stage of unwanted rapid cell proliferation in individuals at risk.

Patients may include but are not limited to primates, especially humans, domesticated companion animals such as dogs, cats, horses, and livestock such as cattle, pigs, sheep, with dosages as described herein.

Compounds of the present invention may be useful for the treatment and/or prevention of conditions and disorders associated with cell proliferation (including cancer, such as brain cancer). Accordingly, the present invention also relates to a method of treating or preventing a proliferative disorder in a patient including administration to the patient of a therapeutically effective amount of a compound of formula (I), or a pharmaceutically-acceptable salt, solvate, hydrate or prodrug thereof. The present invention also relates to the use of a therapeutically effective amount of a compound of formula (I), or a pharmaceutically-acceptable salt, solvate, hydrate or prodrug thereof, for treating or preventing a proliferative disorder. The present invention also provides a pharmaceutical composition for use in treating or preventing a proliferative disorder, in any of the embodiments described in the specification. The present invention also relates to the use of a therapeutically effective amount of a compound of formula (I), or a pharmaceutically acceptable salt, solvate, hydrate or prodrug thereof, for the manufacture of a medicament for treating or preventing a proliferative disorder.

The present invention also relates to a compound of formula (I), or a pharmaceutically acceptable salt, solvate, hydrate or prodrug thereof, when used in a method of treating or preventing a proliferative disorder. The present invention also relates to a composition having an active ingredient for use in treating or preventing a proliferative disorder, wherein the active ingredient is a compound of formula (I), or a pharmaceutically acceptable salt, solvate, hydrate or prodrug thereof. The present invention also relates to the use of a pharmaceutical composition containing a compound of the formula (I), or a pharmaceutically acceptable salt, solvate, hydrate or prodrug thereof, in treating or preventing a proliferative disorder, such as described above. In one embodiment, the compound of formula (I) is essentially the only active ingredient of the composition. In one embodiment, the proliferative disorder is a cancer. In one embodiment, the cancer is a brain cancer (e.g. a solid tumour).

The compounds of formula (I) according to the present invention, and pharmaceutical compositions thereof, may be used in the treatment or prevention of proliferative diseases, preferably cancer. The compounds and compositions of the invention may be useful for the treatment of a wide variety of cancers (tumours), including but not limited to, solid tumours, such as for example, brain cancer, breast cancer, lung cancer, prostate cancer, ovarian cancer, uterine cancer brain cancer, skin cancer, colon cancer and bladder cancer.

The type of cancer or tumor cells that may be amenable to treatment according to the invention include, for example, breast, colon, lung, and prostate cancers, gastrointestinal cancers including esophageal cancer, stomach cancer, colorectal cancer, polyps associated with colorectal neoplasms, pancreatic cancer and gallbladder cancer, cancer of the adrenal cortex, ACTH-producing tumor, bladder cancer, brain cancer (including those discussed below), Ewing's sarcoma, head and neck cancer including mouth cancer and larynx cancer, kidney cancer including renal cell carcinoma, liver cancer, lung cancer including small and non-small cell lung cancers, malignant peritoneal effusion, malignant pleural effusion, skin cancers including malignant melanoma, tumor progression of human skin keratinocytes, squamous cell carcinoma, basal cell carcinoma, and hemangiopericytoma, mesothelioma, Kaposi's sarcoma, bone cancer including osteomas and sarcomas such as fibrosarcoma and osteosarcoma, cancers of the female reproductive tract including uterine cancer, endometrial cancer, ovarian cancer, ovarian (germ cell) cancer and solid tumors in the ovarian follicle, vaginal cancer, cancer of the vulva, and cervical cancer, breast cancer (small cell and ductal), penile cancer, retinoblastoma, testicular cancer, thyroid cancer, trophoblastic neoplasms, and Wilms' tumor. In one embodiment, the cancer is primary. In one embodiment, the cancer is metastatic. In one embodiment, the cancer is benign. In one embodiment, the cancer is malignant.

In one embodiment, the proliferative disorder to be treated and/or prevented is brain cancer. The brain cancer may be selected from anaplastic astrocytoma, astrocytoma, central neurocytoma, choroid plexus carcinoma, choroid plexus papilloma, choroid plexus tumour, diffuse intrinsic pontine glioma, dysembryoplastic neuroepithelial tumour, ependymal tumour, fibrillary astrocytoma, giant-cell glioblastoma, glioblastoma multiforme, gliomatosis cerebri, gliosarcoma, hemangiopericytoma, medulloblastoma, medulloepithelioma, meningeal carcinomatosis, neuroblastoma, neurocytoma, oligoastrocytoma, oligodendroglioma, optic nerve sheath meningioma, paediatric ependymoma, pilocytic astrocytoma, pinealoblastoma, pineocytoma, pleomorphic anaplastic neuroblastoma, pleomorphic xanthoastrocytoma, primary central nervous system lymphoma, sphenoid wing meningioma, subependymal giant cell astrocytoma, subependymoma and trilateral retinoblastoma. Therefore, preferably, the brain cancer is a tumour (preferably, a solid tumour). The brain cancer may be a primary cancer (e.g. a glioma, a meningioma, a pituitary adenoma or a nerve sheath tumour) or a metastatic cancer (i.e. a brain cancer that has arisen as a result of cancer in other parts of the body, such as melanoma or lung cancer).

Alternatively, or in addition to, the compounds may be administered in combination with other agents, for example, chemotherapeutic or immune-stimulating drugs or therapeutic agents.

The terms "combination therapy" or "adjunct therapy" in defining use of a compound of the present invention and one or more other pharmaceutical agents, are intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations of each agent.

In accordance with various embodiments of the present invention one or more compounds of formula (I) may be formulated or administered in combination with one or more other therapeutic agents. Therefore, in accordance with various embodiments of the present invention, one or more compounds of formula (I) may be included in combination treatment regimens with surgery and/or other known treatments or therapeutic agents, such as other anticancer agents, in particular, chemotherapeutic agents, radiotherapeutic agents, and/or adjuvant or prophylactic agents.

There are large numbers of antineoplastic agents available in commercial use, in clinical evaluation and in pre-clinical development, which could be selected for treatment of cancers or other neoplasias by combination drug chemotherapy. Such anti-neoplastic agents fall into several major categories, namely, antibiotic-type agents, antimetabolite agents, hormonal agents, immunological agents, interferon-type agents and a category of miscellaneous agents. Alternatively, other anti-neoplastic agents, such as metallomatrix proteases inhibitors may be used. Suitable agents which may be used in combination therapy will be recognized by those of skill in the art. Suitable agents are listed, for example, in the Merck Index, An Encyclopaedia of Chemicals, Drugs and Biologicals, 12th Ed., 1996.

Combination regimens may involve the active agents being administered together, sequentially, or spaced apart as appropriate in each case. Combinations of active agents including compounds of the invention may be synergistic.

The co-administration of compounds of formula (I) may be effected by a compound of formula (I) being in the same unit dose as a chemotherapeutic or other anti-cancer agent, or the compound of formula (I) and the chemotherapeutic or other anti-cancer agents may be present in individual and discrete unit doses administered at the same, or at a similar time. Sequential administration may be in any order as required, and may require an ongoing physiological effect of the first or initial compound to be current when the second or later compound is administered, especially where a cumulative or synergistic effect is desired.

For various applications, the compounds of the invention can be labelled by isotopes, fluorescence or luminescence markers, antibodies or antibody fragments, any other affinity label like nanobodies, aptamers, peptides etc., enzymes or enzyme substrates. These labelled compounds of this invention are useful for mapping the location of receptors in vivo, ex vivo, in vitro and in situ such as in tissue sections via autoradiography and as radiotracers for positron emission tomography (PET) imaging, single photon emission computerized tomography (SPECT) and the like, to characterize those receptors in living subjects or other materials. The labelled compounds according to the present invention may be used in therapy, diagnosis and other applications such as research tools in vivo and in vitro, in particular the applications disclosed herein.

It will be understood that the invention disclosed and defined in this specification extends to all alternative combinations of two or more of the individual features mentioned or evident from the text or drawings. All of these different combinations constitute various alternative aspects of the invention.

Embodiments of the invention will now be discussed in more detail with reference to the examples which is provided for exemplification only and which should not be considered limiting on the scope of the invention in any way.

EXAMPLES

Synthesis
General Synthetic Route to Heterocycles A&B

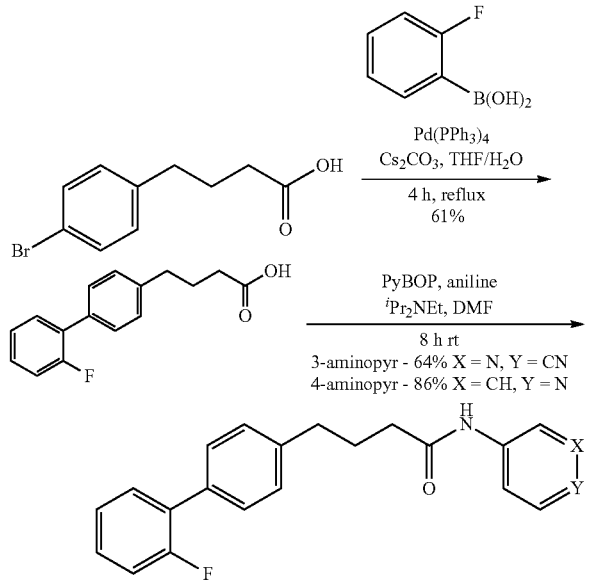

4-(2'-fluoro-[1,1'-biphenyl]-4-yl)butanoic acid

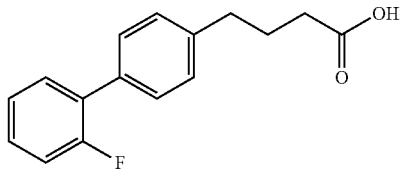 [SMILES: O=C(O)CCCc1ccc(-c2ccccc2F)cc1]

Tetrakis(triphenylphosphine)palladium(0) (590 mg, 0.51 mmol) was added to a stirred suspension of 2-fluorophenylboronic acid (1.7 g, 12.3 mmol), $Cs_2CO_3$ (9.9 g, 30.6 mmol) and 4-bromophenylbutanoic acid (2.50 g, 10.2 mmol) in dry degassed THF/water (100 mL, 9:1 v/v mixture) and the resultant mixture stirred at reflux for 8 hours. The resultant solution was diluted with HCl (100 mL, 1 M (aq)) and extracted with EtOAc (3×50 mL) the combined organic phases subsequently washed with brine, before being dried ($MgSO_4$), filtered and concentrated under reduced pressure. The resultant acid was purified by flash column chromatography (silica, 1:1 v/v EtOAc:Hex) to give the title compound as a white crystalline solid (1.6 g, 61%).

$^1$H NMR (300 MHz, DMSO-$d_6$) δ 12.06 (br s, 1H), 7.57-7.23 (m, 8H), 2.64 (t, J=7.4 Hz, 2H), 2.25 (t, J=7.4 Hz, 2H), 1.88-1.80 (m, 2H). $^{13}$C NMR (75 MHz, DMSO-$d_6$) δ 174.2, 159.1 (d, J=245.8 Hz), 141.3, 132.6, 130.7 (d, J=3.7 Hz), 129.3 (d, J=8.5 Hz), 128.7 (d, J=3.0 Hz), 128.6, 128.2 (d, J=13.9 Hz), 124.9 (d, J=3.7 Hz), 116.0 (d, J=22.6 Hz), 34.1, 33.1, 26.2. $^{19}$F NMR (282 MHz, DMSO) δ−118.4. IR (diamond cell, neat) $v_{max}$: 3026, 2902, 1696, 1480, 1435, 1250, 1202, 939, 799, 756, 563 cm$^{-1}$. LRMS (−ESI) m/z: 257 [(M-H)$^−$, 100%]

4-(2'-fluoro-[1,1'-biphenyl]-4-yl)-N-(pyridin-3-yl)butanamide (WJA69b)

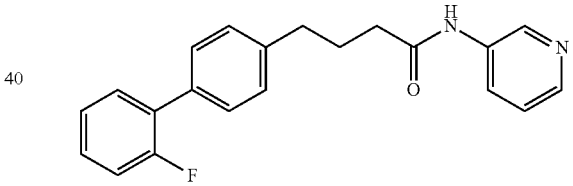

An ice-cold magnetically stirred solution of 4-(2'-fluoro-[1,1'-biphenyl]-4-yl)butanoic acid (200 mg, 0.77 mmol), 3-aminopyridine (80 mg, 0.85 mmol) and $^i$Pr$_2$NEt (268 µL, 1.54 mmol) in DMF (5 mL) was treated with PyBOP® (400 mg, 0.77 mmol), allowed to warm to room temperature and stirring continued for 12 h. The reaction mass was diluted with $CH_2Cl_2$ (50 mL) and water (50 mL), the separated organic phase was subsequently washed with NaHCO$_3$ (25 mL of a sat. aq. solution) and brine (100 mL) before being dried (MgSO$_4$), filtered and purified via flash column chromatography (silica, 1:1 v/v EtOAc:Hex) to give the title compound as a white solid (169 mg, 64%)

$^1$H NMR (400 MHz, DMSO-$d_6$) δ 10.11 (s, 1H), 8.73 (d, J=2.6 Hz, 1H), 8.23 (dd, J=4.7, 1.5 Hz, 1H), 8.03 (ddd, J=8.3, 2.5, 1.6 Hz, 1H), 7.56-7.45 (m, 3H), 7.44-7.36 (m, 1H), 7.36-7.25 (m, 5H), 2.69 (t, J=7.5 Hz, 2H), 2.39 (t, J=7.5 Hz, 2H), 1.95 (p, J=7.5 Hz, 2H). $^{13}$C NMR (101 MHz, DMSO-$d_6$) δ 171.5, 159.1 (d, J=245.6 Hz), 144.0, 141.4, 140.7, 135.9, 132.7, 130.7 (d, J=3.5 Hz), 129.3 (d, J=8.4 Hz), 128.8 (d, J=2.9 Hz), 128.7, 128.2 (d, J=13.2 Hz), 126.0, 124.9 (d, J=3.6 Hz), 123.6, 116.1 (d, J=22.6 Hz), 35.6, 34.3, 26.4. $^{19}$F NMR (282 MHz, DMSO) δ−118.4. IR (diamond cell, neat) $v_{max}$: 3252, 1688, 1582, 1545, 1481, 1420, 1277, 1169, 1026, 798, 753, 701, 561 cm$^{-1}$. LRMS (+ESI) m/z: 335 [(M+H)$^+$, 25%], 357 [(M+Na)$^+$, 100%].

4-(2'-fluoro-[1,1'-biphenyl]-4-yl)-N-(pyridin-4-yl)butanamide (WJA69c)

An ice cold magnetically stirred solution of 4-(2'-fluoro-[1,1'-biphenyl]-4-yl)butanoic acid (200 mg, 0.77 mmol), 4-aminopyridine (80 mg, 0.85 mmol) and $^i$Pr$_2$NEt (268 µL, 1.54 mmol) in DMF (5 mL) was treated with PyBOP® (400 mg, 0.77 mmol), allowed to warm to room temperature and stirring continued for 12 h. The reaction mass was diluted with CH$_2$Cl$_2$ (50 mL) and water (50 mL), the separated organic phase was subsequently washed with NaHCO$_3$ (25 mL of a sat. aq. solution) and brine (100 mL) before being dried (MgSO$_4$), filtered and purified via flash column chromatography (silica, 1:1 v/v EtOAc:Hex) to give the title compound as a white solid (228 mg, 86%).

$^1$H NMR (400 MHz, DMSO-d$_6$) δ 11.92 (s, 1H), 8.67 (d, J=7.2 Hz, 2H), 8.16 (d, J=7.3 Hz, 2H), 7.53-7.42 (m, 3H), 7.37-7.23 (m, 5H), 2.73-2.64 (m, 2H), 2.58 (t, J=7.3 Hz, 2H), 2.02-1.92 (m, 2H). $^{13}$C NMR (101 MHz, DMSO-d$_6$) δ 173.8, 159.1 (d, J=245.6 Hz), 153.0, 142.0, 141.2, 132.7, 131.1, 130.6 (d, J=3.4 Hz), 129.3 (d, J=8.4 Hz), 128.7 (d, J=2.9 Hz), 128.1 (d, J=13.2 Hz), 124.9 (d, J=3.6 Hz), 116.1 (d, J=22.5 Hz), 114.2, 36.2, 34.1, 25.9. $^{19}$F NMR (282 MHz, DMSO) δ –118.4. IR (diamond cell, neat) $v_{max}$: 2926, 1716, 1561, 1500, 1483, 1313, 1135, 823, 754, 514 cm$^{-1}$. LRMS (+ESI) m/z: 335 [(M+H)$^+$, 100%], 357 [(M+Na)$^+$, 40%].

General Synthetic Route to Heterocycles C&D

Summary of Synthetic Route to WJA88

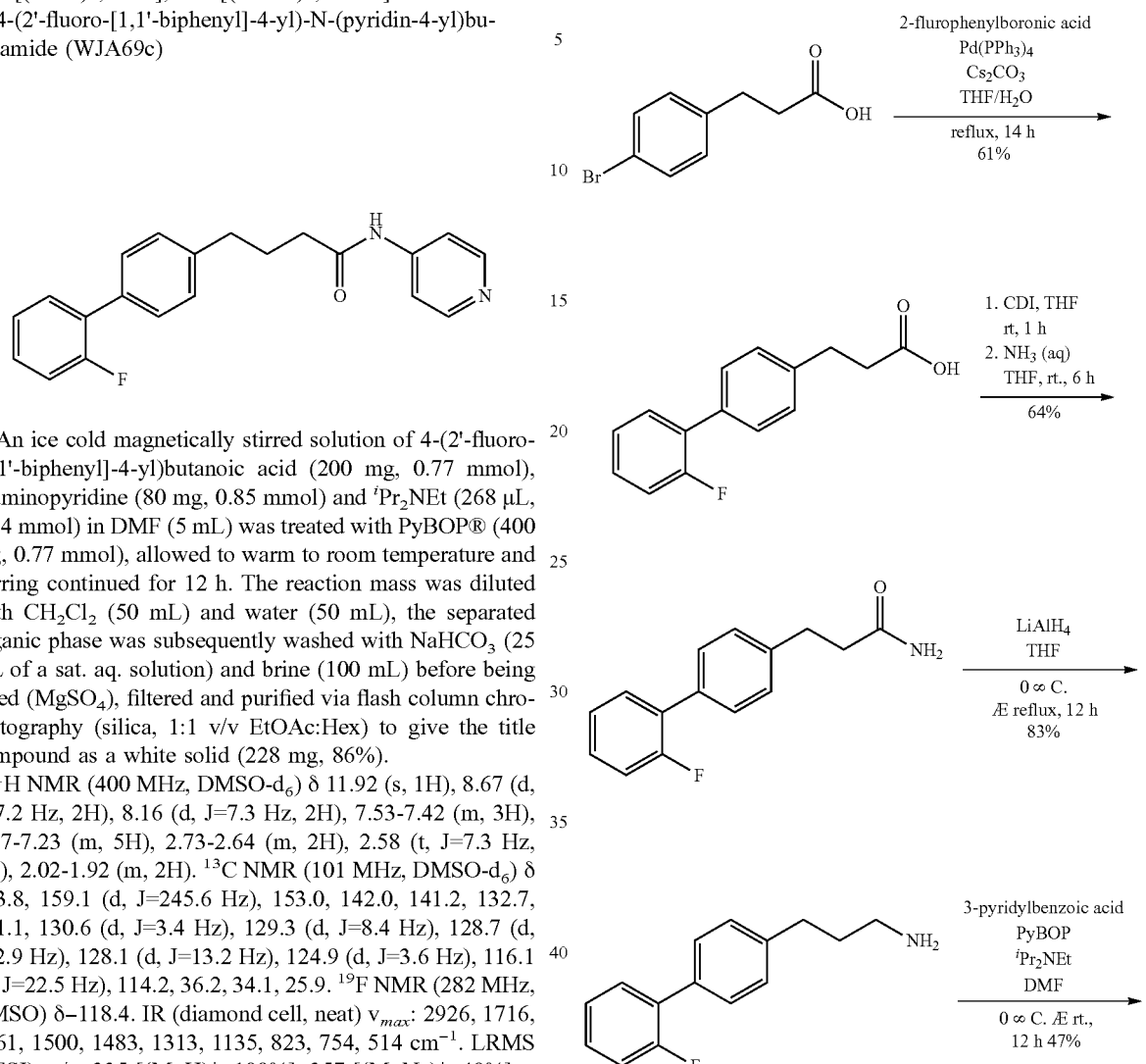

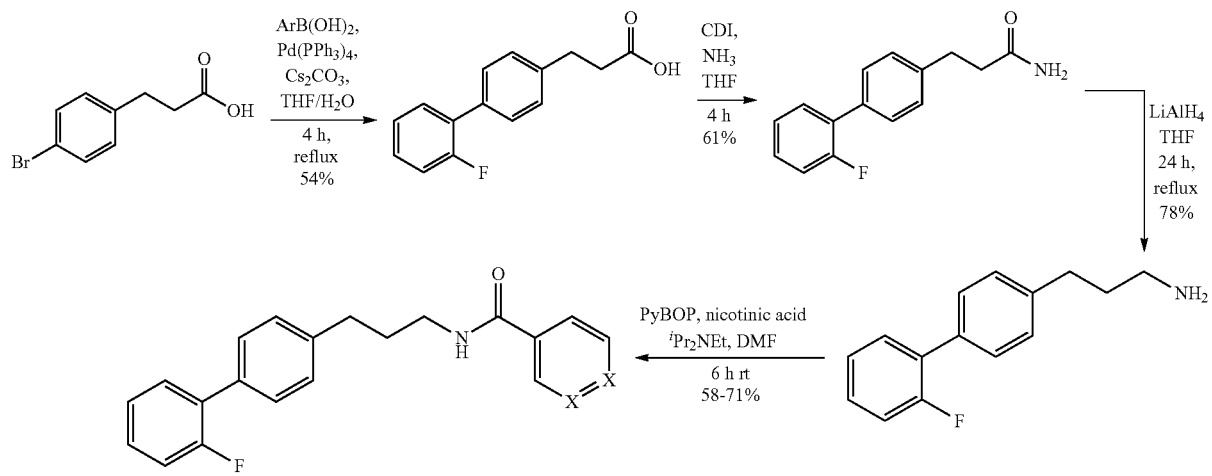

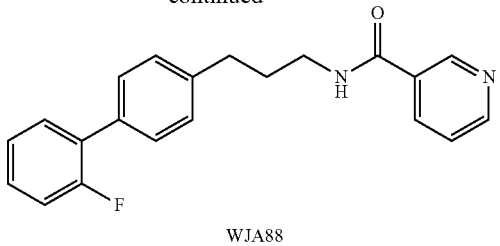

WJA88

3-(2'-Fluoro-[1,1'-Biphenyl]-4-yl)Propanoic Acid

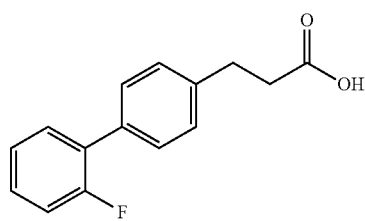 [SMILES: O=C(O)CCc1ccc(-c2ccccc2F)cc1]

Tetrakis(triphenylphosphine)palladium(0) (554.7 mg, 0.48 mmol) was added to a stirred suspension of 2-fluorophenylboronic acid (1.61 g, 11.5 mmol), $Cs_2CO_3$ (11.2 g, 34.5 mmol) and 4-bromophenylpropionic acid (2.2 g, 9.6 mmol) in dry degassed THF/water (100 mL, 9:1 v/v mixture) and the resultant mixture stirred at reflux for 8 hours. The resultant solution was diluted with HCl (100 mL, 1 M (aq)) and extracted with EtOAc (3×50 mL) the combined organic phase was subsequently washed with brine, before being dried ($MgSO_4$), filtered and concentrated under reduced pressure. The resultant acid was purified by flash column chromatography (silica, 1:1 v/v EtOAc:Hex) to give the title compound as a white crystalline solid (1.3 g, 54%).

$^1$H NMR (300 MHz, DMSO-$d_6$) δ 12.16 (br s, 1H), 7.58-7.16 (m, 8H), 2.88 (t, J=7.8 Hz, 2H), 2.67-2.54 (m, 2H). $^{13}$C NMR (75 MHz, DMSO-$d_6$) δ 173.7, 159.1 (d, J=245.7 Hz), 140.6, 132.8, 130.6 (d, J=6.0 Hz), 129.3 (d, J=7.9 Hz), 128.7, 128.5, 128.1 (d, J=12.3 Hz), 124.9 (d, J=3.6 Hz), 116.0 (d, J=22.6 Hz), 35.0, 30.0. $^{19}$F NMR (282 MHz, DMSO) δ–118.4. IR (diamond cell, neat) $v_{max}$: 3187, 1696, 1483, 1410, 1216, 1009, 940, 814, 755, 666, 566, cm$^{-1}$. LRMS (–ESI) m/z: 243 [(M-H)$^-$, 100%]

3-(2'-Fluoro-[1,1'-Biphenyl]-4-yl)Propanamide

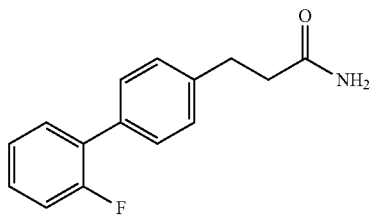 [SMILES: NC(=O)CCc1ccc(-c2ccccc2F)cc1]

3-(2'-fluoro-[1,1'-biphenyl]-4-yl)propanoic acid (1.0 g, 4.1 mmol) and 1,1'-carbonyldiimidazole (854 mg, 5.2 mmol) were stirred for 1 h at room temperature in THF (4 mL) under a N2 atmosphere. The reaction was cooled on ice then aqueous ammonia (28%, 2.25 mL) was added. The reaction was stirred for 4 h, allowing the solution to warm to room temperature. The solvent was removed by rotary evaporation and the residue dissolved in dichloromethane (15 mL) and washed with aqueous sodium hydroxide (1 M, 5 mL), then aqueous hydrochloric acid (1 M, 5 mL) and then water (5 mL). The organic layer was dried (MgSO4), filtered and evaporated to dryness to yield the title compound as a white powder (607 mg, 61%).

$^1$H NMR (300 MHz, DMSO-$d_6$) δ 7.57-7.17 (m, 8H), 6.79 (s, 2H), 2.86 (t, J=7.9 Hz, 2H), 2.41 (t, J=7.9 Hz, 2H). $^{13}$C NMR (75 MHz, DMSO-$d_6$) δ 173.3, 157.4 (d, J=246.3 Hz), 141.2, 132.6, 130.5 (d, J=7.9 Hz), 129.2 (d, J=8.3 Hz), 128.6, 128.4, 128.1 (d, J=12.1 Hz), 124.8, 116.0 (d, J=22.7 Hz), 36.4, 30.5. $^{19}$F NMR (282 MHz, DMSO) δ –118.4. IR (diamond cell, neat) $v_{max}$: 3400, 3180, 1650, 1482, 1412, 1009, 806, 754, 624 cm$^{-1}$. LRMS (+ESI) m/z: 266 [(M+Na)$^+$, 100%].

3-(2'-Fluoro-[1,1'-Biphenyl]-4-yl)Propan-1-Amine

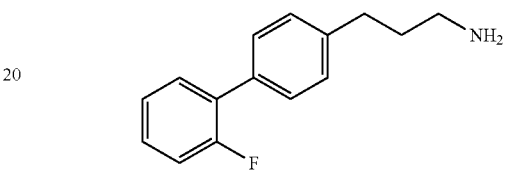

A solution of amide (500 mg, 2.1 mmol) in THF (8 mL) was treated with LiAlH$_4$ (312 mg, 8.2 mmol) at 0 ° C. and stirred under a N$_2$ atmosphere whilst warming to room temperature. After 2 h, the reaction was heated at reflux for 16 h and then cooled on ice. Chilled H2O (300 μL) was added dropwise, with vigorous stirring, and then followed by aqueous sodium hydroxide (15% w/v, 300 μL) and additional water (1 mL). The solution was left stirring at room temperature until effervescence had ceased and the grey powder had turned white (30 min). The solution was dried (MgSO4) and then filtered. The precipitate was washed with additional dichloromethane (2×10 mL). The filtrate in each case was combined, and solvent removed under reduced pressure. The crude oil thus obtained was purified by flash column chromatography (silica, 0.5:9.5 v/v MeOH(saturated with NH$_3$):CH$_2$Cl$_2$) to give the title compound as a colourless wax (375 mg, 78%).

$^1$H NMR (400 MHz, DMSO-$d_6$) δ 7.60-7.12 (m, 8H), 4.17 (br s, 2H), 3.05-2.88 (m, 2H), 2.75-2.52 (m, 2H), 1.77-1.64 (m, 2H). $^{19}$F NMR (282 MHz, DMSO) δ–118.4. IR (diamond cell, neat) $v_{max}$: 3334, 2923, 1611, 1481, 1314, 814, 751, 551cm$^{-1}$. LRMS (+ESI) m/z: 230 [(M+Na)$^+$, 100%].

N-(3-(2'-Fluoro-[1,1'-Biphenyl]-4-yl)Propyl)Nicotinamide (WJA88)

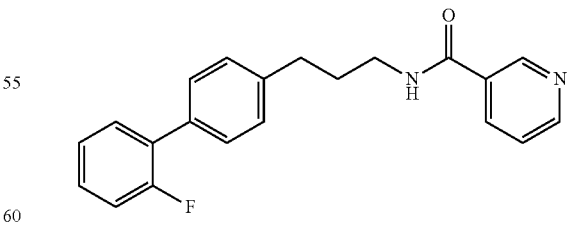

An ice-cold magnetically stirred solution of 3-(2'-fluoro-[1,1'-biphenyl]-4-yl)propan-1-amine (200 mg, 0.87 mmol), nicotinic acid (129 mg, 1.04 mmol) and $^i$Pr$_2$NEt (303 μL, 1.74 mmol) in DMF (5 mL) was treated with PyBOP® (452 mg, 0.87 mmol), allowed to warm to room temperature and stirring continued for 12 h. The reaction mass was diluted with CH$_2$Cl$_2$ (50 mL) and water (50 mL), the separated organic phase was subsequently washed with NaHCO$_3$ (25 mL of a sat. aq. solution) and brine (100 mL) before being dried (MgSO$_4$), filtered and purified via flash column chromatography (silica, EtOAc).

$^1$H NMR (400 MHz, DMSO-d$_6$) δ 9.03 (d, J=1.5 Hz, 1H), 8.73-8.66 (m, 1H), 8.19 (dt, J=7.9, 2.0 Hz, 1H), 7.73-7.42 (m, 4H), 7.40-7.15 (m, 5H), 3.42-3.30 (m, 2H), 2.70 (t, J=7.6 Hz, 2H), 1.95-1.85 (m, 2H).

$^{13}$C NMR (101 MHz, DMSO-d$_6$) δ 164.8, 159.1 (d, J=245.6 Hz), 151.7, 148.3, 141.4, 134.86, 132.6, 130.6 (d, J=3.5 Hz), 130.1, 129.2 (d, J=8.2 Hz), 128.7 (d, J=2.9 Hz), 128.6, 128.2, 126.5 (d, J=11.6 Hz), 124.8 (d, J=3.4 Hz), 123.4, 32.6, 32.3, 30.6. $^{19}$F NMR (282 MHz, DMSO) δ-118.4. IR (diamond cell, neat) v$_{max}$: 3302, 3027, 2948, 2465, 1626, 1588, 1544, 1481, 1448, 1431, 1406, 1362, 1317, 1211, 820, 757, 742, 708, 697, 622, 535 cm$^{-1}$. LRMS (+ESI) m/z 357 [(M+Na)$^+$, 100%].

Biological Evaluation

Tubulin Polymerization Assay

Fluorescence-based tubulin polymerization assay was conducted in a final volume of 55 µL using the Tubulin Polymerization Assay kit (Cytoskeleton, Colo., USA) as per manufacturer's instructions. Briefly, porcine brain tubulin was incubated with test compounds at 37° C. and fluorescence was measured using with Tecan M200 PRO+ microplate reader (Tecan, Switzerland) at 355 nm excitation and 460 nm emission.

Figure 2:
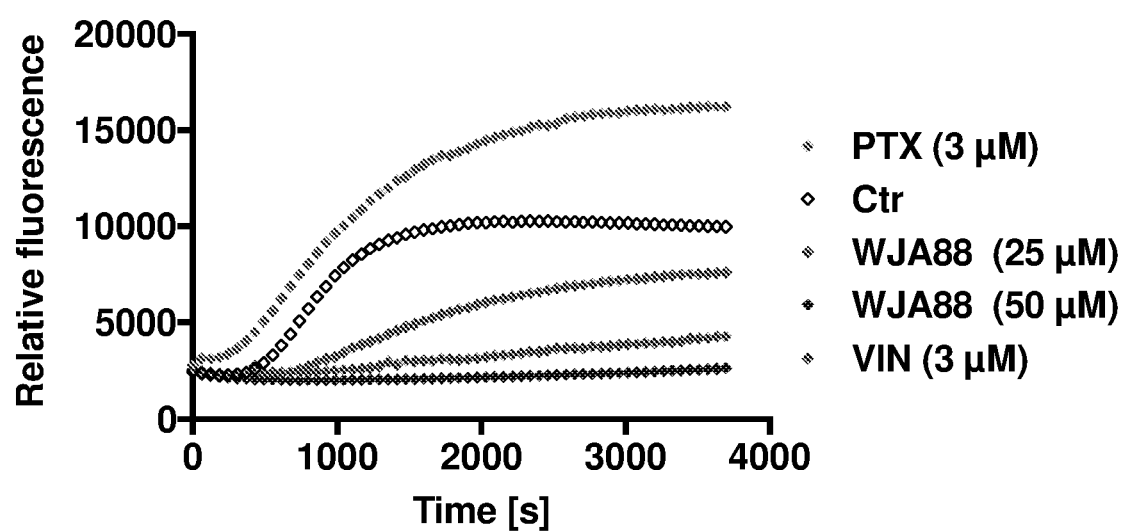
FIG. 2. Results of an in vitro tubulin polymerization assay using WJA88.

Compared to control (DMSO), paclitaxel (PTX) enhanced tubulin polymerization, whereas vinblastine (VIN), WJA69b and WJA88 inhibited tubulin polymerization (see FIG. 1 and FIG. 2).

Metabolic Stability Assay

Figure 3:
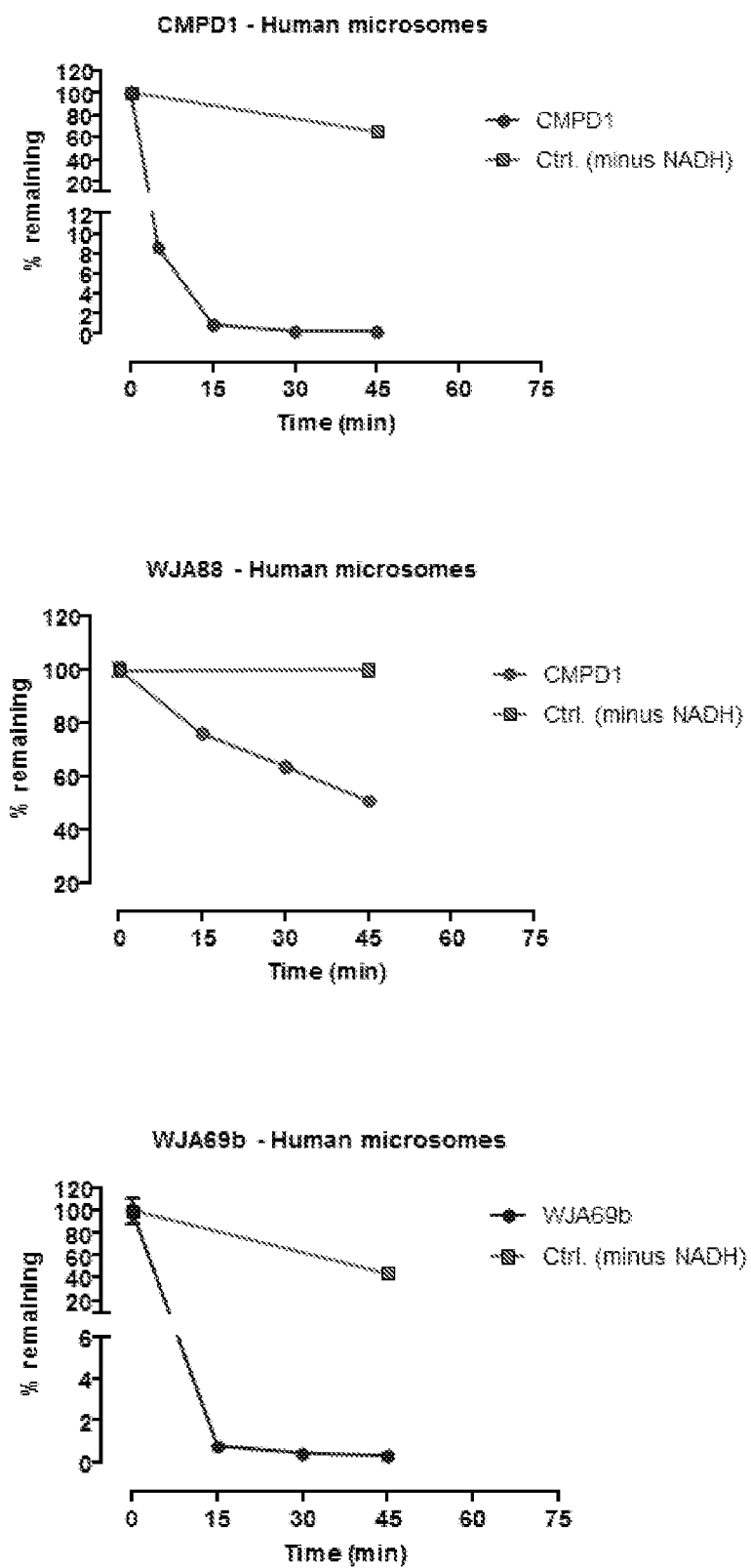
FIG. 3. Metabolic stability test of CMPD1, WJA69b and WJA88.

All reactions were performed in 200 µl reaction volume in duplicates. 10 µM of WJA85 were incubated with human microsomes (0.4 mg/ml) in potassium phosphate buffer (0.1 M, pH 7.4) at 37° C. with gentle shaking for 5 mins. Assay was started by adding 12 µl of NADPH regenerating system (containing final concentrations of 1 mM NADP, 3.0 mM glucose-6-phosphate, 3.3 mM MgCl$_2$ and 0.4 u/ml glucose-6-phosphate dehydrogenase). Reaction was quenched by adding 130 µl of ice cold methanol, vortexed vigorously and centrifuged at 15000 g at 4° C. for 10 mins. Supernatant was collected for analysis and 5 µl was analysed using LC/MS/MS (see below).The results are shown in FIG. 3. Negative controls include reaction mix, without addition of NADPH regenerating system and reaction mix with inactive microsomes (heat inactivated at 80° C. for 30 mins).

The LC-MS analysis was performed on an Agilent 1260 LC system coupled to a QTRAP 6500 mass spectrometer. For LC, zorbax Extend-C18 (2.1×50 mm 1.8 um) column was used in reversed-phase mode at flow rate of 200 µl/min, with gradient elution starting with 10% of phase B (0.1% formic acid in water) and 90% of phase A (0.1% formic acid in acetonitrile). The amount of phase B was linearly increased from 10% to 90% in 5 minutes followed by 2 mins at 90% B then back to initial conditions at 8 minutes.

The MS detector was operated with an ESI positive ionization mode. Source temperature and capillary voltage were set at 300° C. and 4000 V respectively. The Analyst software was used to control the instruments and data acquisition. Assaying of mitotic inhibitors was carried out utilizing the mode of multiple reaction monitoring (MRM) using the following conditions for each compound. Ion transitions were 350.3 to 241 for CMPD1, 335 to 106 for WJA88, and 335 to 185 for WJA69b. Fragmentor voltage was set to 145 V with collision energy of 30 for all the compounds.

Clonogenic Assay

Figure 4:
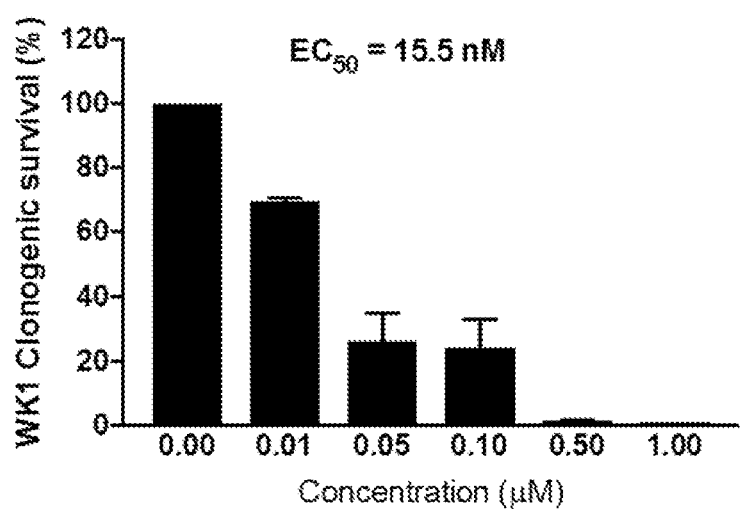
FIG. 4. Cellular efficacy of WJA88 in the clonogenic assay.

WK1 (2×10$^4$ cells/well) were plated onto Matrigel matrix coated (1:50; Corning, USA) 6-well plates. Cells were treated the following day with WJA88 at various concentrations, in duplicates and incubated for 14 days at 37° C., 5% CO$_2$. Cells were then washed with phosphate buffered saline and stained with Toluidine Blue solution (50% w/v in 50% v/v methanol) for 45 min at 4° C. Stain was removed and cells were washed with water and left to dry before being imaged with Gel-Doc XR Imager (Biorad Laboratories, USA). Images were analysed with ImageJ software (NIH, USA) using the Colony Area plugin to reflect the percentage of cell confluence in each well. Cell confluence was then normalised to control wells and non-linear regression (Graphpad PRISM, USA) was used to determine the EC$_{50}$. Data are mean±SEM from two independent experiments. The results are shown in FIG. 4.

3D Spheroid Assay

Figure 5:
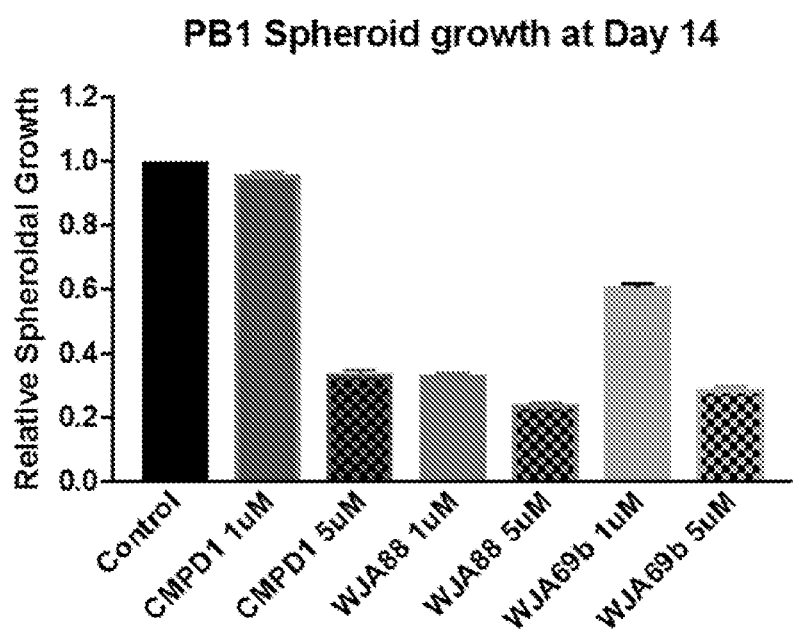
FIG. 5. Cellular efficacy of compounds in 3D spheroid assay.

PB1 cells (8×10$^4$ cells/well) were plated onto 0.8% v/v agarose coated, flat bottom, 96-well plates and left to form spheroids for 48-72 h. After spheroid formation, individual spheroids were imaged at 5× or 10× objective in bright field using a ZEISS AXIO Vert.A1 (Carl Zeiss, Germany) and these images were taken as Day 0. Spheroids were then treated with test compounds at various concentrations, in duplicates and were imaged at day 14. Individual spheroid images at day 0 and day 14 were analysed for spheroid area (µm$^2$) using ImageJ Software (NIH, USA). Fold change in spheroid area over time was calculated as a measure of spheroid growth. Data mean±SEM from two independent experiments. The results are shown in FIG. 5.

CMPD1 has the following structure:

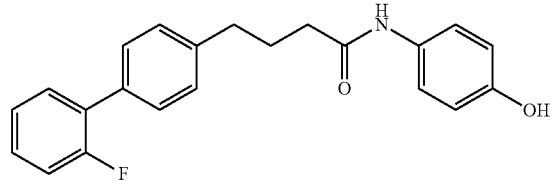 [SMILES: O=C(CCCc1ccc(-c2ccccc2F)cc1)Nc1ccc(O)cc1]

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A compound of formula (I):

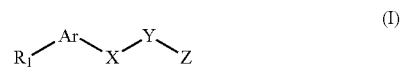

or a pharmaceutically acceptable salt or prodrug thereof, wherein:

X is C$_3$ alkyl or C$_3$ alkenyl;

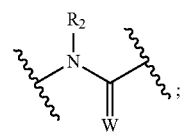

Y is

W is O;

R₂ is H, alkyl or alkenyl;

Z is heteroaryl group, which heteroaryl is optionally substituted with a hydroxyl, a halo group or a heteroalkyl group;

R₁ is phenyl, which is optionally substituted with a halo group or a heteroalkyl group;

Ar is phenyl, wherein R₁ and X are para to each other around the phenyl of Ar.

2. The compound according to claim 1 or a pharmaceutically acceptable salt or prodrug thereof, wherein R₂ is H.

3. The compound according to claim 1 or a pharmaceutically acceptable salt or prodrug thereof, wherein the R₁ is a phenyl substituted with a halo group or a heteroalkyl group.

4. The compound according to claim 3, wherein the halo group is F.

5. The compound according to claim 1 or a pharmaceutically acceptable salt or prodrug thereof, wherein Z is a monocyclic or bicyclic heteroaryl group.

6. The compound according to claim 5 or a pharmaceutically acceptable salt or prodrug thereof, wherein the heteroaryl group includes one or more nitrogen atoms.

7. The compound according to claim 5 or a pharmaceutically acceptable salt or prodrug thereof, wherein Z is pyridine.

8. The compound according to claim 7 or a pharmaceutically acceptable salt or prodrug thereof, wherein the nitrogen of the pyridine is at the meta position.

9. A pharmaceutical composition comprising a compound of formula (I) according to claim 1 or a pharmaceutically acceptable salt or prodrug thereof, together with a pharmaceutically acceptable excipient.

10. A compound or a pharmaceutically acceptable salt thereof, wherein the compound is selected from the group consisting of:

| Compound | Structure |
| --- | --- |
| WJA88 | 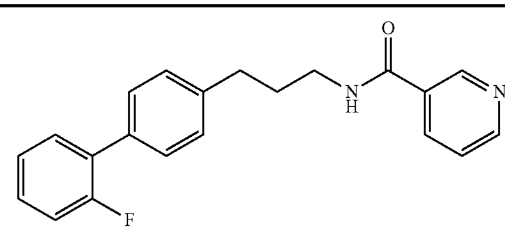 |
| 2 | 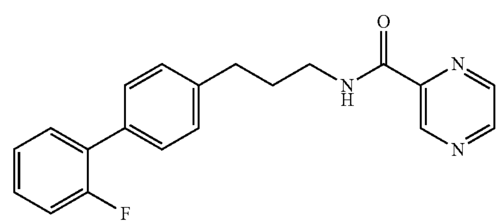 [SMILES: O=C(NCCCc1ccc(-c2ccccc2F)cc1)c1cnccn1] |
| 3 | 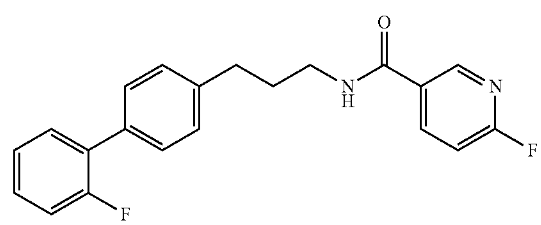 [SMILES: O=C(NCCCc1ccc(-c2ccccc2F)cc1)c1ccc(F)nc1] |
| 4 | 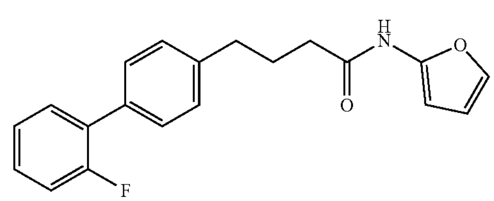 [SMILES: O=C(CCCc1ccc(-c2ccccc2F)cc1)Nc1ccco1] |
| 5 | 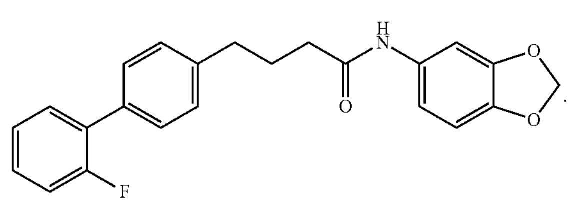 [SMILES: O=C(CCCc1ccc(-c2ccccc2F)cc1)Nc1ccc2c(c1)OCO2] |

11. The compound according to claim 1 having the following structure:
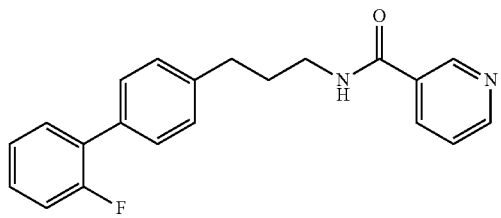 [SMILES: O=C(NCCCc1ccc(-c2ccccc2F)cc1)c1cccnc1]
or a pharmaceutically acceptable salt thereof.
* * * * *